United States Patent
Pitts-Baggett et al.

(10) Patent No.: US 10,458,886 B2
(45) Date of Patent: Oct. 29, 2019

(54) APPARATUS AND METHOD FOR SIMULTANEOUS SAMPLING OF MATERIAL AT MULTIPLE DEPTHS

(71) Applicant: NUCOR CORPORATION, Charlotte, NC (US)

(72) Inventors: April Danielle Pitts-Baggett, Northport, AL (US); Paul Andrew Turner, Milwaukee, WI (US)

( * ) Notice: Subject to any disclaimer, the term of this patent is extended or adjusted under 35 U.S.C. 154(b) by 8 days.

(21) Appl. No.: 15/445,207

(22) Filed: Feb. 28, 2017

(65) Prior Publication Data
US 2017/0248499 A1    Aug. 31, 2017

Related U.S. Application Data

(60) Provisional application No. 62/301,491, filed on Feb. 29, 2016.

(51) Int. Cl.
*G01N 1/12*    (2006.01)

(52) U.S. Cl.
CPC .................... *G01N 1/125* (2013.01)

(58) Field of Classification Search
CPC .. G01N 1/125; C21C 5/4673; A61B 17/1703; G01K 13/125; C21B 7/24; B22D 1/005
USPC ............................. 73/864.53, 864.59; 266/99
See application file for complete search history.

(56) References Cited

U.S. PATENT DOCUMENTS

| | | |
|---|---|---|
| 3,816,383 A | 6/1974 | Stotko |
| 3,905,238 A * | 9/1975 | Falk .................. G01N 1/1409 |
| | | 73/864.54 |
| 4,538,794 A * | 9/1985 | Scherff ................. C21C 5/4673 |
| | | 266/226 |
| 5,014,561 A | 5/1991 | Falk et al. |
| 5,131,633 A | 7/1992 | Brinker |
| 8,479,579 B2 | 7/2013 | Neyens et al. |
| 2014/0318276 A1 * | 10/2014 | Cappa .................... G01N 1/125 |
| | | 73/863.11 |

FOREIGN PATENT DOCUMENTS

WO    WO2014146917 A1    9/2014

OTHER PUBLICATIONS

SU500489, Jan. 1976, pp. 1-5.*

* cited by examiner

*Primary Examiner* — John Fitzgerald
*Assistant Examiner* — Truong D Phan
(74) *Attorney, Agent, or Firm* — Moore & Van Allen PLLC; Jeffrey R. Gray

(57) ABSTRACT

Embodiments of the present invention relate to a sampling apparatus having one or more support structures and two or more sampling molds operatively coupled to the one or more support structures. The two or more sampling molds may be sealed or unsealed. The sampling apparatus is pressurized with a gas and immersed in the molten metal. The two or more sampling molds become unsealed when the mold stops at least partially melt. When the sampling apparatus is depressurized the one or more unsealed sampling molds capture one or more molten metal samples. The sampling apparatus is removed from the molten metal and the samples are removed from the sampling molds and analyzed.

20 Claims, 11 Drawing Sheets

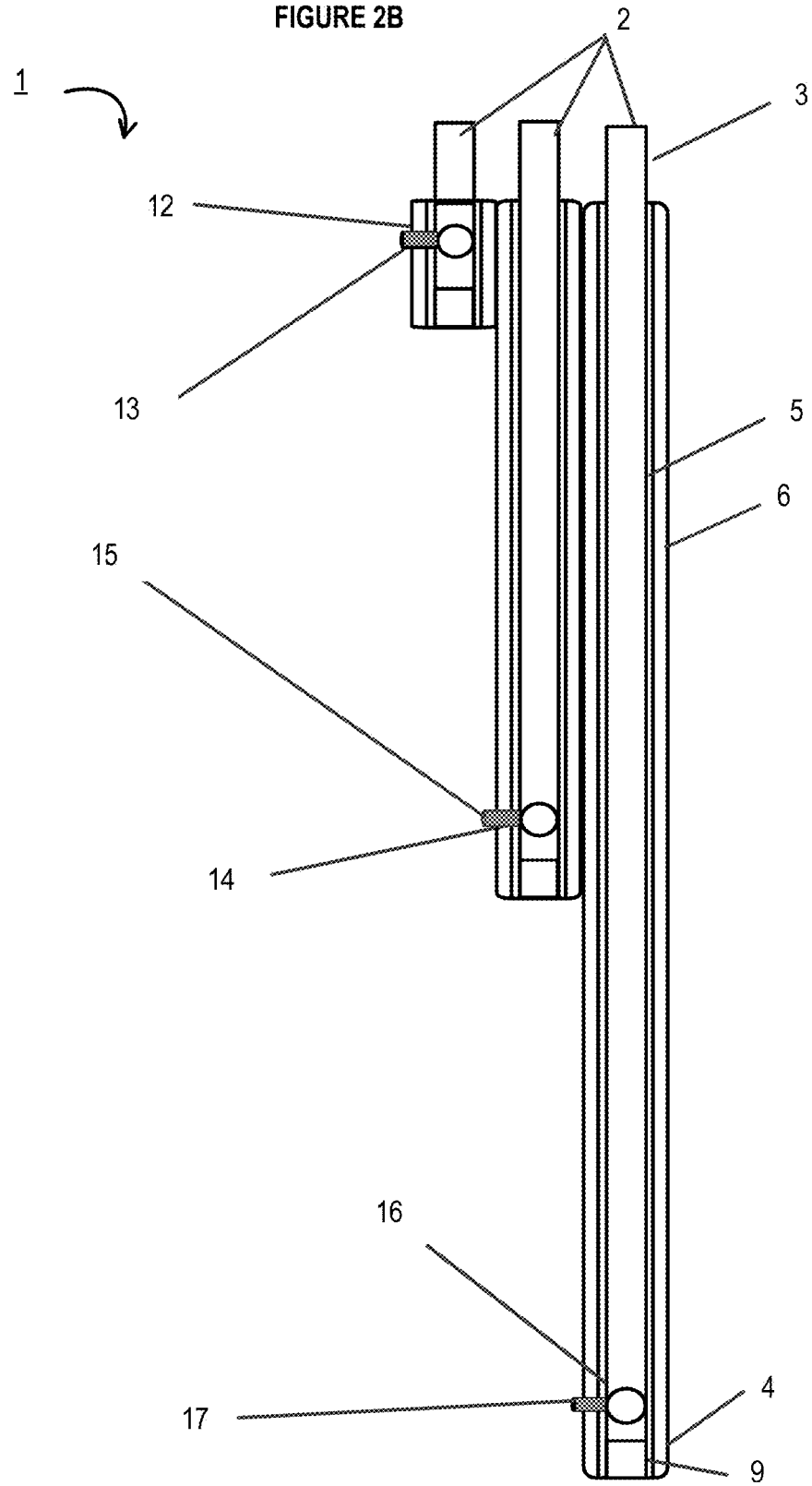

of incl

>10 μm

APPARATUS AND METHOD FOR SIMULTANEOUS SAMPLING OF MATERIAL AT MULTIPLE DEPTHS

CLAIM OF PRIORITY UNDER 35 U.S.C. § 119

The present Application for a Patent claims priority to U.S. Provisional Patent Application Ser. No. 62/301,491 entitled "Apparatus and Method for Simultaneous Sampling of Steel at Multiple Depths" filed on Feb. 29, 2016 and assigned to the assignees hereof and hereby expressly incorporated by reference herein.

FIELD

The present disclosure relates to an apparatus, and method of using an apparatus, to sample molten metal at different depths. More specifically, the present invention relates to a sampler apparatus with two or more sampler molds, which are used to capture multiple samples of molten metal from different distances within steelmaking equipment, such as a ladle within a ladle metallurgy facility (LMF).

BACKGROUND

Due to the high temperatures and pressure of molten metal within the steelmaking process it is difficult to obtain samples of the molten metal. Moreover, the equipment used in the steel making process limits the areas from which samples may be taken. Some sampler apparatuses may be utilized to capture a single sample of molten steel near the interface of the slag-steel; however, it is currently not possible to capture multiple molten steel samples from multiple depths within steelmaking equipment, such as from a ladle within the LMF.

SUMMARY

Embodiments of the present invention are related to a sampling apparatus having two or more sampling molds operatively coupled to a support structure. It should be understood that in some embodiments of the invention, the two or more sampling molds may be located within a single support structure, or each of the two or more sampling molds may be located within multiple support structures. The one or more support structure may have a single hollow portion, or multiple hollow portions, that communicate with each of the two or more sampling molds. The two or more sampling molds may be sealed, such as through the use of one or more mold stops. In other embodiments, one or more of the sampling molds are unsealed, while one or more of the sampling molds are sealed. The sampling apparatus is pressurized with a gas and immersed in the molten metal. After immersion to the desired depth, the sampling apparatus is depressurized, the one or more mold stops are unsealed by the molten metal, and the two or more unsealed sampling molds capture the molten metal samples. The sampling apparatus is then removed from the molten metal. This process may take less than 10, 7, 5, or 3 seconds. Thereafter, the captured molten metal samples are allowed to cool to solidification, the samples are removed from the sampling molds of the sampling apparatus, and the samples are analyzed.

The sampling apparatus of the present invention is utilized to simultaneously obtain samples of molten steel at the desired depths, without contaminating the samples from the sampling apparatus itself, and while being able to utilize the sampling apparatus with the existing ports in the existing steelmaking equipment, such as the ladle. The samples are analyzed and can be utilized to determine the cleanliness of the steel and to improve processing techniques for manufacturing steel, including to improve the cleanliness of the steel.

The LMF process, which will be described in further detail later generally includes transferring the steel from an electric arc furnace (EAF) to the ladle, performing a heat killed process and building slag, adding alloys to achieve the desired steel composition, desulfurization of the molten metal, pre-rinse, performing a calcium treatment, and post-rinse. With respect to the heat killed process the steel in the ladle is deoxidized to in order to produce a more uniform finished steel product. In an aluminum killed process within the LMF, the formation of alumina is inevitable, Equation 1 below illustrates the reaction for forming alumina. Alumina formation primarily occurs early in the process due to removing oxygen from the steel that was added at the electric arc furnace (EAF), but the formation of alumina can happen all the way through the LMF process up until the material is cast if any oxygen is reintroduced to the ladle. Desulfurization is another process that is critical to the LMF process. This occurs early in the heat, and is typically shown to occur by Equation 2 below; however, this process can only occur after the oxygen has been removed from the heat or the heat has been "killed."

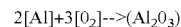

$$2[Al]+3[O_2] \text{-->} (Al_2O_3) \qquad 1$$

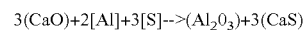

$$3(CaO)+2[Al]+3[S] \text{-->} (Al_2O_3)+3(CaS) \qquad 2$$

The slag-steel interface is typically considered a critical area of reactions within the LMF. The viscosity, thickness, coherency, and composition of the slag can play a large role in the cleanliness of a LMF heat. As a result, slags have been studied to understand these key components. Throughout the processing time at the LMF, slag characteristics change due to the reactions that occur and component additions being made. Early in the heat, the desired slag should be very fluid in conjunction with a vigorous stir which leads to a very large slag steel interface, which is key for the desulfurization process. After the sulfur has been removed, it is typical to see changes in the viscosity as well as the thickness of the slag layer. The pre-rinse period usually starts after the sulfur removal has been verified. During this time, the slag is optimized for inclusion capture, primarily alumina based inclusions. The stir is not vigorous, but rather it is gentle, causing only a small, stable open eye in the slag. The limited eye and small wave action help reduce the potential for reoxidation and the creation of more alumina. Calcium wire (Calcium wire or Calcium-Silicon wire) is added at the end of pre-rinse to modify the remaining alumina based inclusions to transform them into liquid inclusions at casting temperatures. The desired result is a fully modified inclusion population with sufficient calcium to compensate for a subsequent mild reoxidation event, without causing the presence of excessive amounts of calcium sulfides. While the slag samples can be easily captured and studied, capturing samplings at different depths within the molten metal below the slag has not been possible.

Improving control of steel cleanliness through secondary steel refining can translate to higher quality finished product. Steel sampling plays an important role in the determination and impact of the refining process on steel cleanliness. The present sampling apparatus and the method of using the sampling apparatus described herein provides a more complete picture of the reactions occurring at different depths within the molten metal, and provides additional insight on how the cleanliness of the steel can be improved.

Embodiments of the invention comprise a sampling apparatus, wherein the sampling apparatus is used to take samples of molten material at multiple depths. The sampling apparatus comprises one or more support structures having a first end and a second end, wherein the second end and at least a portion of the one or more support structures are configured for immersion within molten material. The sampling apparatus further comprises two or more sampling molds operatively coupled to the one or more support structures and configured for immersion within the molten material. The sampling apparatus is configured for operative coupling with a gas source in order to pressurize the sampling apparatus with a gas to prevent premature capture of the molten material samples in the two or more sampling molds.

In further accord with embodiments of the invention the molten material is molten metal. In other embodiments of the invention the one or more support structures comprise an internal support, and an external cover. In yet other embodiments of the invention, the internal support comprises a metal tube, and the external cover comprises a paperboard tube.

In still other embodiments of the invention the two or more sampling molds at least comprise an upper sampling mold that is sealed with an upper mold stop, a lower sampling mold that is sealed with a lower mold stop, and wherein the upper sampling mold and lower sampling mold are immersed within the molten material, and capture molten material when the molten material at least partially melts the upper mold stop and the lower mold stop and the gas is stopped.

In further accord with embodiments of the invention, the two or more sampling molds at least comprise an upper sampling mold that is sealed with an upper mold stop, a lower sampling mold that is unsealed, and wherein the upper sampling mold and the lower sampling mold are immersed within the molten material, and capture the molten material samples when the molten material at least partially melts the upper mold stop and the gas is stopped.

In other embodiments of the invention, the one or more sampling molds at least comprise a first sampling mold, a second sampling mold, a third sampling mold, and wherein the third sampling mold is immersed deeper than the second sampling mold and the second sampling mold is immersed deeper than the first sampling mold, wherein the first sampling mold, the second sampling mold, and the third sampling mold capture molten steel samples when the gas source is stopped.

In yet other embodiments of the invention, the one or more support structures further comprise a refractory on the outside of the one or more support structures. In still other embodiments of the invention, the one or more support structures are a single support structure that is operatively coupled to the two or more sampling molds. In other embodiments of the invention, the one or more support structures are at least two support structures operatively coupled together, and wherein each of the at least two support structures comprise a single sampling mold.

Another embodiment of the invention comprises a sampling apparatus, wherein the sampling apparatus is used to take samples of molten material at multiple depths. The sampling apparatus comprises one or more support structures having a first end and a second end and two or more sampling molds operatively coupled to the one or more support structures, wherein the two or more sampling molds comprise at least an upper sampling mold sealed with an upper mold stop and a lower sampling mold sealed with a lower mold stop. The sampling apparatus is configured for operative coupling with a gas source in order to pressurize the sampling apparatus with a gas to prevent premature capture of samples from the molten material in the two or more sampling molds. Moreover, the second end and at least a portion of the one or more support structures are configured for immersion within molten material such that the upper sampling mold and the lower sampling mold are submerged within the molten material at different depths, and wherein the two or more sampling molds capture the samples from the molten material when the molten material at least partially melts the two or more mold stops and the gas is stopped.

In further accord with embodiments of the invention, the two or more sampling molds further comprise a middle sampling mold sealed with a middle mode stop, wherein when immersed in the molten material the middle sampling mold is located at a depth between the upper sampling mold and the lower sampling mold Embodiments of the invention further comprise methods for capturing molten material samples. One embodiment comprises pressurizing a sampling apparatus with a gas from a gas source, wherein the sampling apparatus comprises one or more support structures having a first end and a second end and two or more sampling molds operatively coupled to the one or more support structures. The method further comprises immersing the second end of the sampling apparatus in a molten material such that the two or more sampling molds are immersed in the molten material at different depths, depressurizing the sampling apparatus, capturing samples of the molten material in the two or more sampling molds, and removing the sampling apparatus from the molten material.

In further accord with embodiments of the invention, the molten material is molten metal. In other embodiments of the invention, the one or more support structures further comprise an internal support and an external cover. In yet other embodiments of the invention, the internal support comprises a metal tube and the external cover comprises a paperboard tube, and wherein the internal support prevents the sampling apparatus from collapsing on itself due to the pressure of the molten material.

In other embodiments of the invention, the two or more sampling molds at least comprise an upper sampling mold that is sealed with an upper mold stop, a lower sampling mold that is sealed with a lower mold stop, and wherein the upper sampling mold and lower sampling mold are immersed within the molten material and capture molten material when the molten material at least partially melts the upper mold stop and the lower mold stop and the gas is stopped.

In yet other embodiments of the invention, the one or more sampling molds at least comprise an upper sampling mold that is sealed with an upper mold stop, a lower sampling mold that is unsealed, and wherein the upper sampling mold and the lower sampling mold are immersed within the molten material and capture the molten material samples when the molten material at least partially melts the upper mold stop and the gas is stopped.

In still other embodiments of the invention, the one or more sampling molds at least comprise a first sampling mold, a second sampling mold, a third sampling mold, and wherein the third sampling mold is immersed the deeper than the second sampling mold and the second sampling mold is immersed deeper than the first sampling mold, wherein the first sampling mold, the second sampling mold, and the third sampling mold capture the samples from the molten material when the gas is stopped.

In other embodiments of the invention, the one or more support structures is a single support structure that is operatively coupled to the two or more sampling molds, or are at least two support structures operatively coupled together and wherein each of the at least two support structures comprise at least a single sampling mold.

To the accomplishment of the foregoing and the related ends, the one or more embodiments of the invention comprise the features hereinafter fully described and particularly pointed out in the claims. The following description and the annexed drawings set forth certain illustrative features of the one or more embodiments. These features are indicative, however, of but a few of the various ways in which the principles of various embodiments may be employed, and this description is intended to include all such embodiments and their equivalents.

BRIEF DESCRIPTION OF THE DRAWINGS

The foregoing and other advantages and features of the invention, and the manner in which the same are accomplished, will become more readily apparent upon consideration of the following detailed description of the invention taken in conjunction with the accompanying drawings, which illustrate embodiments of the invention and which are not necessarily drawn to scale, wherein:

FIG. 2B illustrates a cross-sectional view of a sampling apparatus having two or more separate support structures and multiple sampling molds, in accordance with embodiments of the present invention.

DETAILED DESCRIPTION

Embodiments of the present invention now may be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Figure 1:
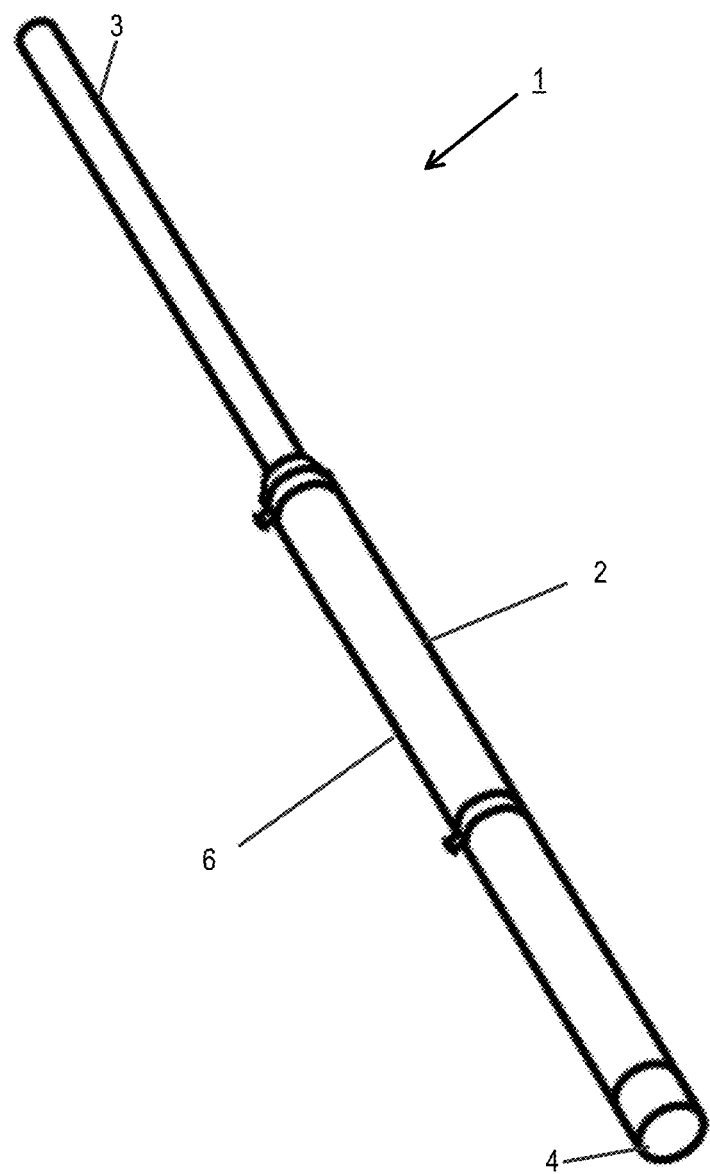
FIG. 1 illustrates a perspective view of a sampling apparatus, in accordance with embodiments of the present invention.
Figure 2A:
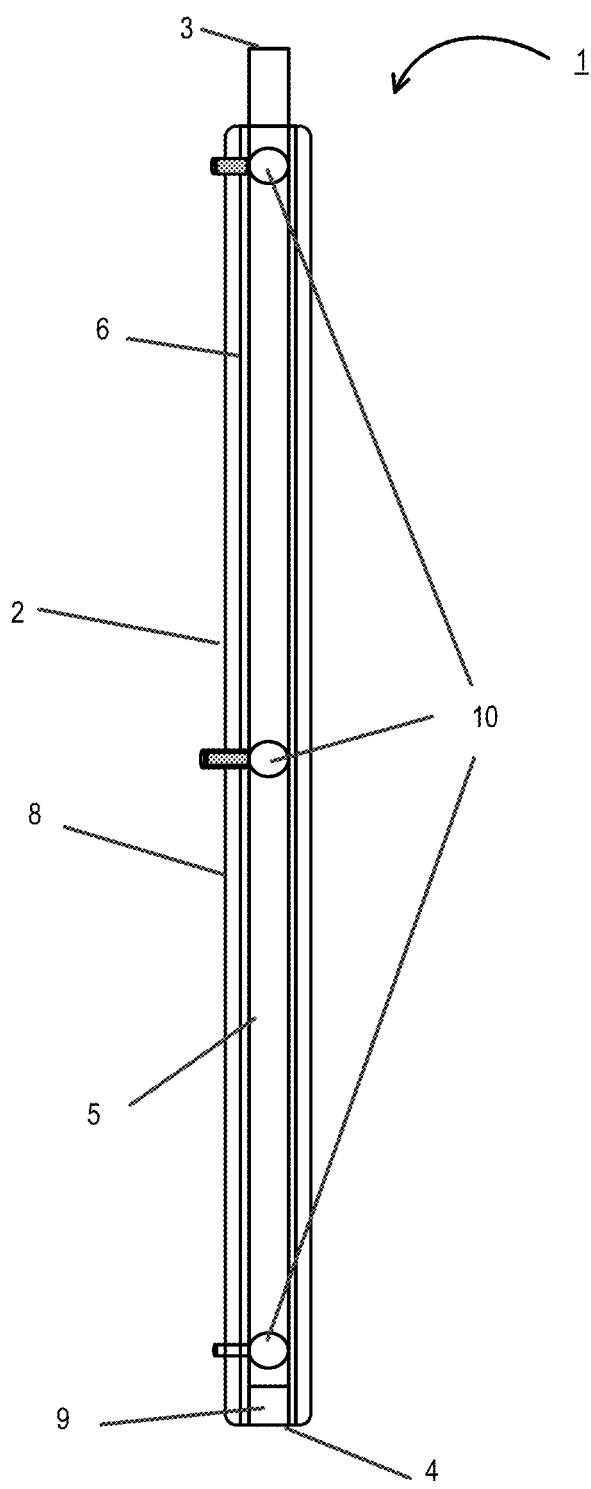
FIG. 2A illustrates a cross-sectional view of the sampling apparatus in FIG. 1 with a single support structure and multiple sampling molds, in accordance with embodiments of the present invention.

FIG. 1 illustrates a perspective view of a sampling apparatus 1, while FIG. 2A illustrates a cross sectional view of the sampling apparatus 1. The sampling apparatus 1 may comprise a support structure 2 (e.g., an elongated bar having one or more hollow portions) that is operatively coupled to the two or more sampling molds 10. The support structure may have a first end (e.g., a secured end 3) and a second end (e.g., an immersion end 4). The support structure 2 may be any type of cross-sectional shape, such as but not limited to a circular, oval, triangular, square, rectangular, or any other type of shape with any number of sides. While the support structure 2 is illustrated as being a linear straight elongated bar, it should be understood that the support structure 2 may be non-linear (e.g., curved, bent, elbows, turns, or the like). As such, the support structure 2 may have many different elongated shapes in order to capture samples from different locations with a vessel. The support structure 2 of the present invention may be made of an internal support 5 and an external cover 6. The internal support 5 may comprise of a conduit of any shape and size that has one or more hollow portions therein (e.g., a hollow tube, a tube with multiple hollow portions, or any other type of conduit). The internal support 5 provides the rigidity required to withstand the necessary immersion depth within the molten metal (e.g., withstand the temperatures, pressure, or the like). The internal support may be made of metal; however, the internal support 5 may be made of any other type of material that can withstand the pressures of the molten metal during immersion. The external cover 6, may be a paperboard cover of any shape or size (e.g., paperboard tube) that is assembled over the internal support 5 to protect the internal support 5 from exposure to the molten metal. It should be understood that the external cover 6 may be made of another type of material. Conventional immersion samplers are designed to be immersed between 18 inches (45 cm) and 24 inches (60 cm) into the steel bath and are constructed of paperboard; however, because of the depths to which the sampling apparatus 1 of the present invention will be used, a paperboard tube would be insufficient to mechanically withstand the buoyant forces exerted on a the sampling apparatus 1 when immersed to the desired depths (e.g., a six foot depth in the molten metal bath, or the like). For example, the molten metal within the ladle may range in temperature from 2700 to 3100 degrees F. (or may be outside of, overlapping, or within this range), and the internal support 5 allows for rigidity required to survive long enough in the molten metal to capture the samples.

In addition to the external cover 6, a non-splash refractory 8 may be added over the external cover 6 to provide additional protection and increase the life of the sampling apparatus 1 when immersed into the molten steel bath, as illustrated in FIG. 2A. The non-splash refractory 8 in some embodiments of the invention is a sleeve composed primarily of RCF fiber (e.g., ceramic fiber). The RCF fiber may be a blend of $SiO_2$ and $Al_2O_3$ ceramic materials bound with a colloidal silica binder; however, it should be understood that any material may be used that will allow for the capture of the sample. In some embodiments, the non-splash refractory 8 is adhered to the external cover 6 (e.g., paperboard tube) of the sampling apparatus 1 in a two-step process: 1) an adhesive refractory mortar is applied to the external cover 6 (e.g., the mating surface of the paperboard tube) and the non-splash refractory 8 is slid on over the external cover 6; and 2) fasteners (e.g., staples, screws, clamps, or other like fasteners) are used to secure the non-splash refractory 8 in place while the adhesive refractory mortar cures (e.g., the fasteners may or may not be removable after the mortar cures).

A support structure stop 9 (e.g., plug, cap, cover, or other component, such as a refractory plug) (otherwise described herein as a "bar seal") may be utilized to seal the support structure 2 at the immersion end 4. It should be understood that the support structure stop 9 may be a refractory plug that is inserted into the support structure 2 to create the seal, another type of plug inserted into the support structure 2, a cap over the support structure 2, a cap or plug that is formed integral within the support structure 2, and/or another feature that seals the immersed end 4 of the sampling apparatus 1.

As illustrated in FIG. 2A the support structure 2 has sampling molds 10 operatively coupled to the support structure at various locations within the support structure 2. An example of a sampling mold is illustrated in FIGS. 4A and 4B. In some embodiments of the invention, there may be at least two or more sampling molds 10 located within the support structure 2. In the illustrated embodiment of FIGS. 2A and 3, three sampling molds 10 are utilized (12, 14, 16). In some embodiments of this invention, the sampling molds 10 may be placed approximately two feet apart from each other, such that molten metal samples may be taken at defined depths with in the molten metal bath. The sampling molds 10 may be operatively coupled to the support structure 2 through openings located within the support structure 2, the external cover 6, and the non-splash refractory 8. The sampling molds 10 may have fill tubes 102 (e.g., of any shape or size, and such fill tube may be an enclosed tube or simply a channel to direct the flow of the molten metal) that protrude through apertures in the internal support 5, external cover 6, and/or the non-splash refractory 8. The sampling molds 10 may be operatively coupled to the support structure 2 in an air tight configuration (e.g., the gas discussed later can only escape through the sampler mold 10), or otherwise may be operatively coupled to the support structure 2 in a configuration that is not air-tight (e.g., the gas can escape through the sampler mold 10 and around the sampler mold 10).

The sampling apparatus 1 illustrated in FIG. 2A has a single cavity within the support structure 2 that is in communication with the two or more sampling molds 10. For example, a portion of the two or more sampling molds 10 are located within the single cavity within the support structure 2, such that the pressurized gas in the single cavity flows around and/or through the two or more sampling molds 10. However, it should be understood that in some embodiments of the invention the support structure 2 may have two or more cavities, and each of the two or more cavities may communicate with a single sampling mold 10. For example, each sampling mold 10 may receive pressurized gas from a single corresponding cavity that may be supplied with gas of a different pressure. As such, the gas provided to each cavity, and thus, each sampling mold 10, may be independently controlled depending on the depth to which the sampling mold 10 may be immersed.

FIG. 2B illustrates another embodiment of the sampling apparatus 1, in which two or more separate support structures 2 are operatively coupled together to form a single sampling apparatus 1. It should be understood that each of the support structures 2 may have components that are similar to the components of the sampling apparatus 1 described with respect to FIGS. 1 and 2A. As such, as illustrated in FIG. 2b two or more support structures 2 are operatively coupled together (e.g., stacked side by side as illustrated, nested with each other in a triangular shape, or the like). Each of the support structure 2 may comprise a first end (e.g., a secured end 3) and a second end (e.g., an immersion end 4). The support structures 2 may be made of an internal support 5 and an external cover 6. In addition to the external cover 6, a non-splash refractory 8 may be added over the external cover 6 to provide additional protection and increase the life of the sampling device when immersed into the molten steel bath. A support structures stop 9 (e.g., plug, cap, cover, or other component, such as a refractory plug) (otherwise described herein as a "bar seal") may be utilized to seal the support structure 2 at the immersion end 4.

As illustrated in FIG. 2B, each support structure 2 within the sampling apparatus 1 has a single sampling mold 10 operatively coupled to the support structure 2 at various locations. Again, an example of a sampling mold is illustrated in FIG. 4. In the illustrated embodiment of FIG. 2B, three sampling molds 10 are utilized (12, 14, 16), each located in a separate support structure 2. In some embodiments of this invention, the sampling molds 10 may be placed approximately two feet apart from each other, such that molten metal samples may be taken at defined depths with in the molten metal bath. The sampling molds 10 may be operatively coupled to each support structure 2 through openings located within the support structure 2, the external cover 6, and the non-splash refractory 8. The sampling molds 10 may have fill tubes as previously described herein.

The sampling apparatus 1 illustrated in FIG. 2B has support structures 2 with a single sampling mold 10 located a different depths and each support structure 2 has a different length. However, it should be understood that in some embodiments of the invention, there may be at least two or more sampling molds 10 located within each of the support structures 2 within the sampling apparatus 1. As such, the sampling apparatus 1 illustrated in FIG. 2B may take samples in the same way as the sampling apparatus 1 illustrated in FIGS. 1-2A. Moreover, it should be further understood that the sampling apparatus 1 illustrated in FIG. 2B may include a combination of two or more support structures 2 each with multiple sampling molds 2 (e.g., two, three, four, or other like number of support structures 2 with multiple sampling molds 10) in order to capture multiple samples at each of the multiple depths at the same time within the molten material.

Figure 3:
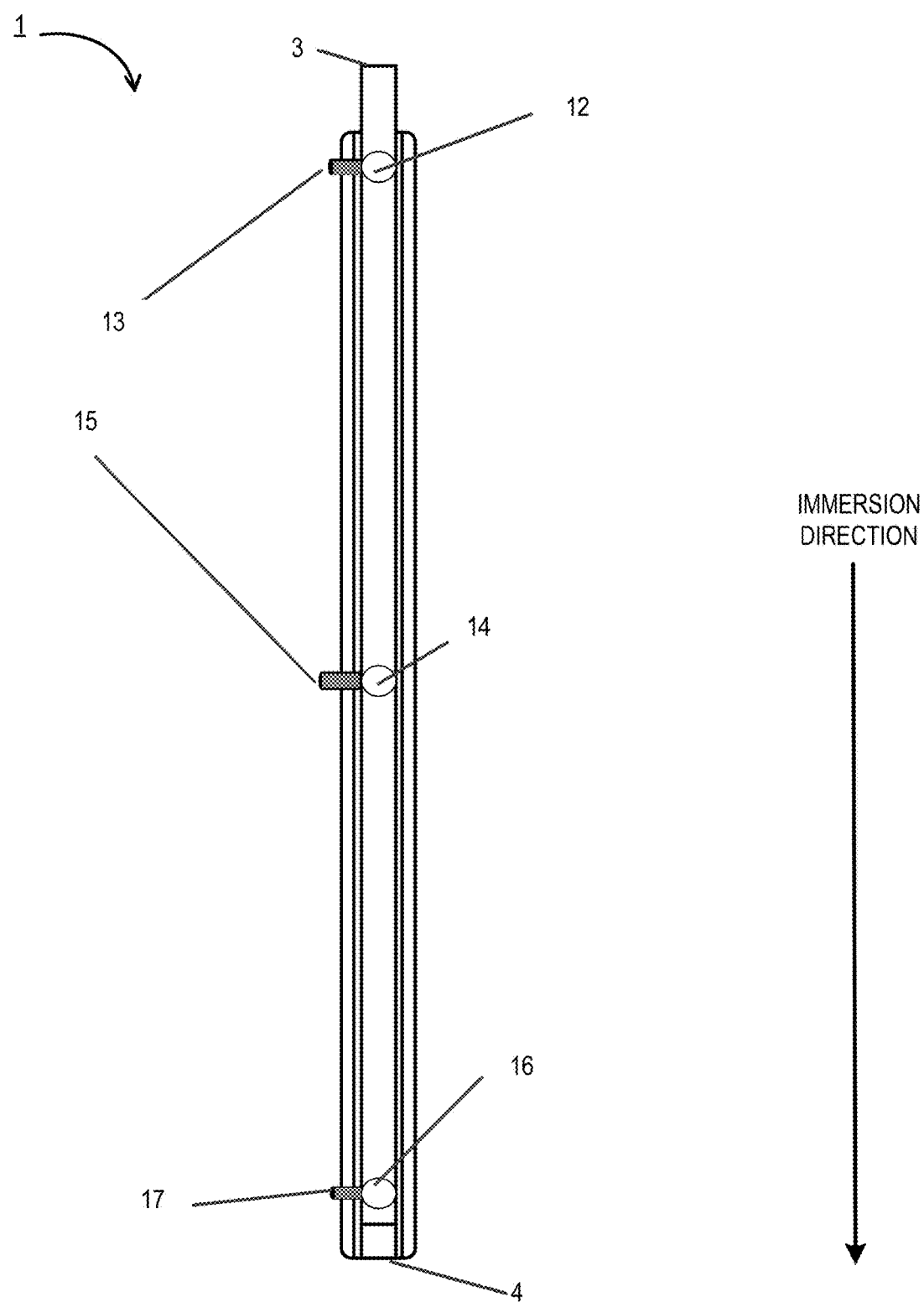
FIG. 3 illustrates a cross-sectional view of the sampling apparatus in FIG. 1 as it would be inserted into the molten metal, in accordance with embodiments of the present invention.
Figure 4A:
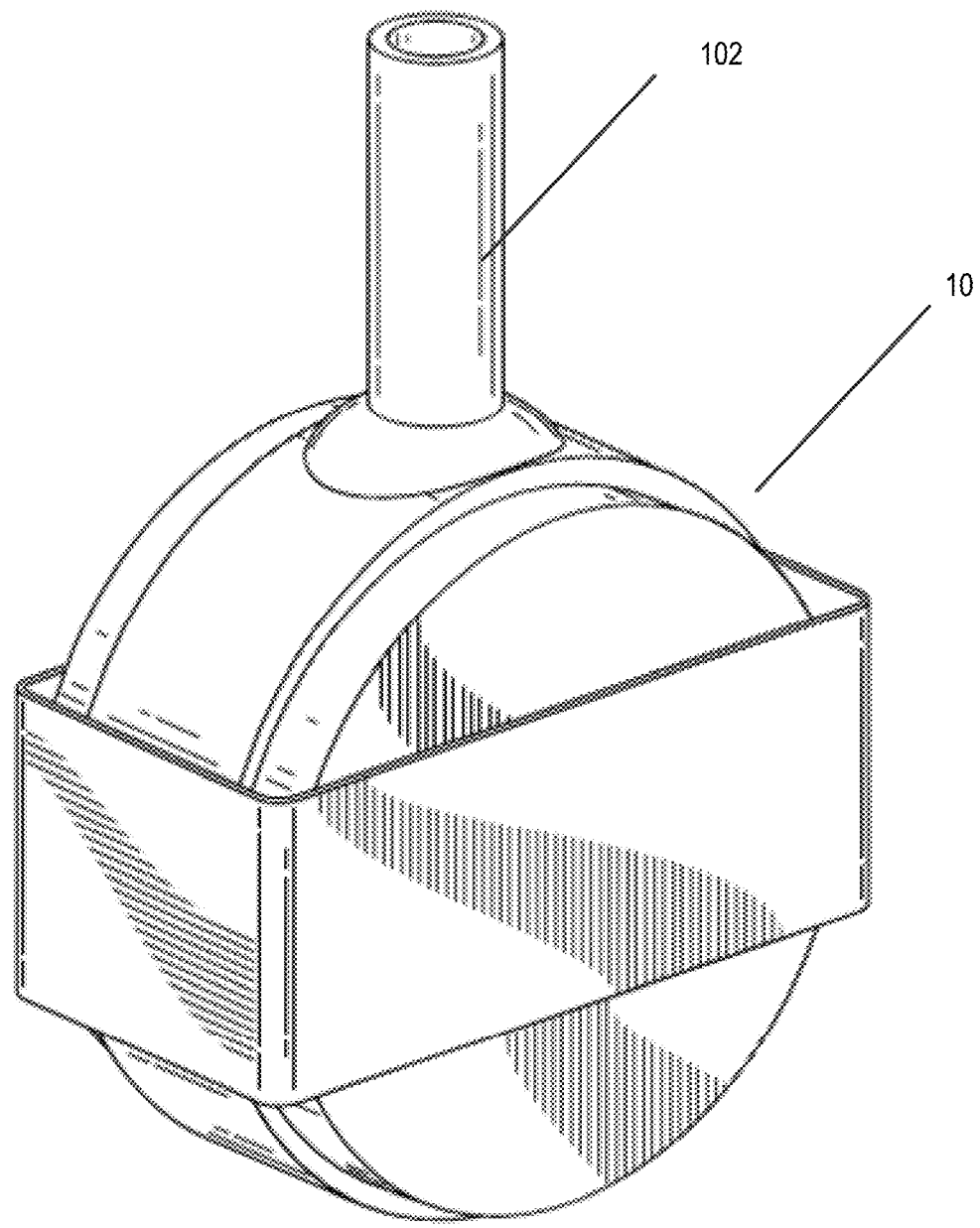
FIG. 4A illustrates a perspective view of a sampling mold of the sampling apparatus, in accordance with embodiments of the present invention.
Figure 4B:
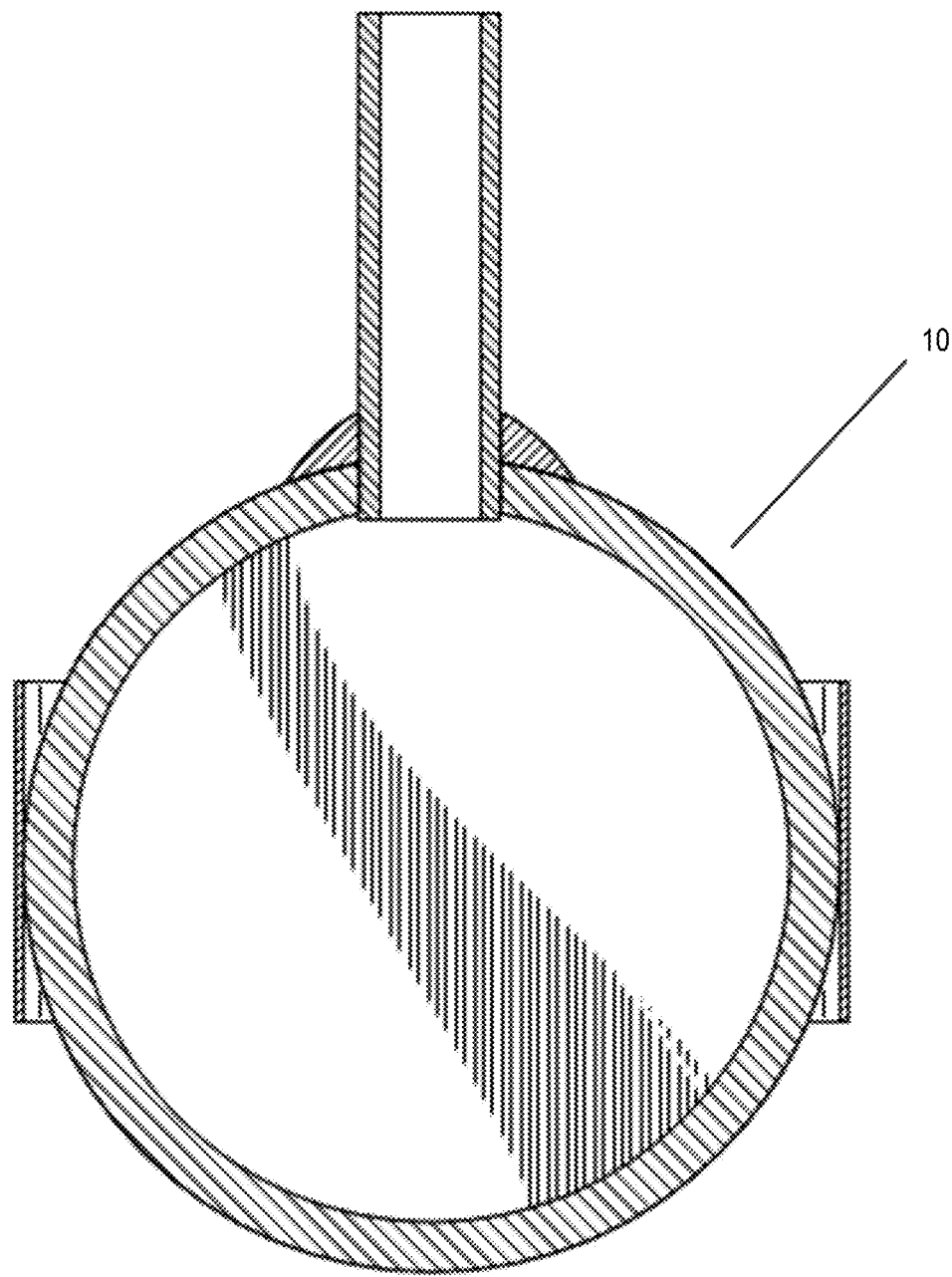
FIG. 4B illustrates a cross-sectional view of the sampling mold of FIG. 4A, in accordance with embodiments of the present invention.

FIG. 3 illustrates how the sampling apparatus 1 may be immersed within the molten material. FIG. 3 illustrates the sampling apparatus 1 illustrated in FIGS. 1 and 2A, but it should be understood the description with respect to FIG. 3 may also apply to the sampling apparatus 1 described with respect to FIG. 2B. The sampling apparatus 1 is immersed approximately 72 inches (185 cm) into the molten steel bath in order to obtain samples at the desired sampling depths of approximately 12 inches (30 cm) (or a range from 0 to 24 inches), 36 inches (91 cm) (or a range from 24 to 48 inches), 60 inches (152 cm) (or a range from 48 to 72 inches) below the slag-steel interface. As such, the sampling apparatus 1 in some embodiments may be over 10 feet long (or range from 8 to 12 feet) in order to reach the desired depths. However, it should be understood that any size sampling apparatus 1 with any number of sampling molds 10 located at any position within the sampling apparatus 1 may be used to capture the desired number of molten metal samples at the desired depths. Generally, as will be described with respect to FIG. 5, the sampling apparatus 1 is pressurized with gas (e.g., argon gas, or the like), such that gas will flow out of any unsealed sampling molds 10 (e.g., unseal before immersion or unsealed when a mold stop melts), and/or around the sampling molds 10 at the locations at which the sampling molds are positioned within the sampling apparatus 1. The mold stops and gas described herein helps to prevent the flow of molten metal into one or more of the sampling molds 10 before the sampling apparatus 1 is located at the desired sampling location. In order to capture the samples, the one or more mold stops at least partially melt to allow molten metal to flow in the sampling mold (e.g., the mold stops melt to a point that at least part of the fill tube of the sampling mold is exposed, or the like), the gas is shut off, the sampling molds 10 fill with molten metal samples, and the sampling apparatus 1 is removed from the molten metal bath. These process steps may all occur within a few seconds (e.g., less than or equal to 10, 7, 5, 3, or the like number of seconds).

To prevent depressurization of the sampling apparatus 1 to atmosphere during the immersion into the molten bath, the sampling apparatus 1 is sized to create the desired pressure and two or more mold stops are utilized to initially plug the fill tubes of the sampling molds 10. With respect to the design of the sampling apparatus 1, the sampling molds 10 and the support structure 2 are sized such that the pressure inside the cavity of the sampling apparatus 1 (or two or more cavities) does not drop below the minimum pressure required to prevent premature filling of the sampling molds 10, and specifically the lowest sampling mold 16, which is immersed to the deepest location within the molten bath.

Moreover, as illustrated in FIG. 3A the fill tubes of the first sampling mold 12 (or upper sampling mold) and second sampling mold 14 (or middle sampling mold), which would not be inserted as far as the third sampling mold 16 (or lower sampling mold), are sealed with a mold stop 13, 15 (e.g., a plug, cap, or other feature that seals the molds) (otherwise described herein as a "mold seal") to prevent the filling tubes 102 of the sampling molds 10 from filling with steel until the mold stops 13, 15 are melted by the molten metal bath. The mold stops may be made of steel, pyrex glass, and/or another material that melts after a defined time period when the mold stops come in contact with the molten material being sampled. The mold stops (e.g., plug, cap, cover, etc.) will at least partially melt away in the steel bath. The reason that one or more of the sampling molds are sealed is that during immersion, the pressurized purge gas (e.g., argon) cannot leak to atmosphere (causing depressurization of the sampler). Once the seals melt in the steel bath, the steel bath creates enough resistance to the flow of purge gas so that the sampling apparatus 1 does not depressurize.

It should be further understood that the third sampling mold 16 (or the lower sampling mold) may also have a mold stop 17. As such, each sampling mold 10 within the sampler apparatus 1 may have a mold stop that seals the sampling molds 10. It should be understood that the mold stops may be the same mold stops (same size and/or melting rate), or two or more of the sealed mold stops may be a different type (e.g., different size and/or melting rate) such that all of the mold stops would melt at the same time. For example, the mold stops may be sized such that the lower mold stop 17 may melt slower than the middle mold stop 15, which may melt slower than the upper mold stop 13. As such, since the lower mold stop 17 is immersed in the molten metal longer than the middle mold stop 15, which are both immersed in the molten metal longer than the upper mold stop 13, the different sizes and/or melting rates would allow the mold stops to melt at the same time, and thus capture samples in the sampler molds 10 at approximately the same time once the gas is shut off.

It should be understood that the sampling apparatus 1 is described herein for use with a ladle in a LMF; however, the sampling apparatus 1, and the method for using the sampling apparatus 1, may be utilized within other equipment of the steelmaking process, such as but not limited to the EAF (e.g., at the tap location, charge location, alloying location, electrode location, or other locations), degasser, tundish, or the like, or utilized within the equipment of other types of manufacturing processes, such as in processing other types of molten materials (other liquid materials), and in particular molten materials that are being processed at elevated temperatures.

Figure 5:
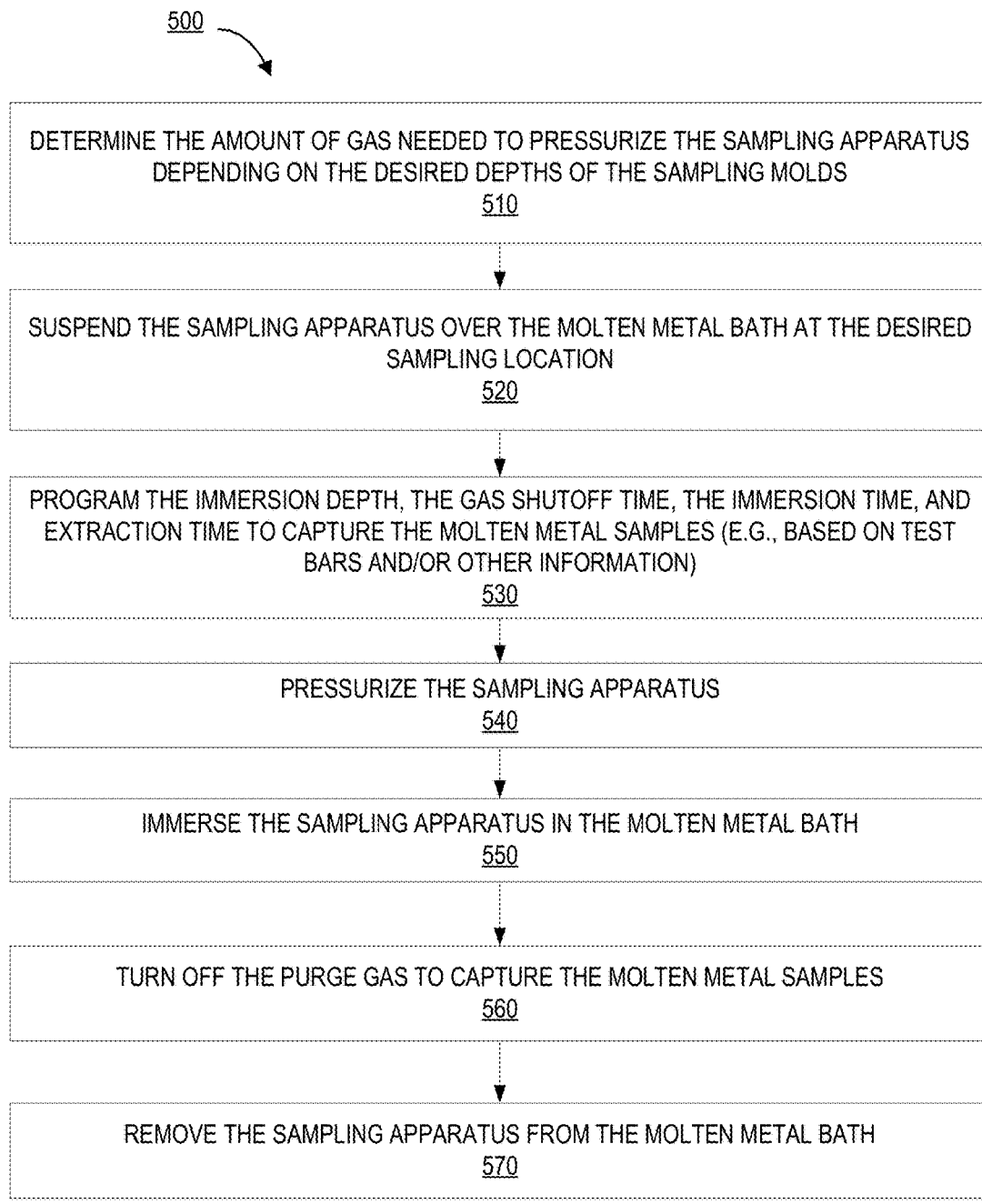
FIG. 5 illustrates a process flow of how the sampling apparatus captures molten metal samples, in accordance with embodiments of the present invention.

FIG. 5 illustrates the process 500 of obtaining samples from a molten metal bath using the sampling apparatus 1. As illustrated by block 510 in FIG. 5, a determination of the amount of gas needed to pressurize the sampling apparatus 1 is made depending on the depths to which the sampling molds are being immersed. Argon gas is preferred as the purge gas; however, other types of gas may be utilized. In order to ensure that the sampling molds 10 of the multi-depth sampling apparatus 1 do not fill until the sampling molds 10 reach the desired sampling depth within the molten metal, the amount of argon gas needed to pressurize the system is calculated. The gauge pressure of the molten metal bath at each desired sampling depth is calculated using Equation 3.

$$P(\text{bar}) = (p_{slag})(g)(h_{slag}) + (p_{steel})(g)(h_{steel}) \quad\quad 3$$

Values used for calculations:

$P_{slag}$=3100 kg/m$^3$ $P_{steel}$=7000 kg/m$^3$ g=9.81 m/s$^2$

Slag thickness ($h_{slag}$)=0.23 m

Steel depth$_{s1}$ ($h_{steel}$)=0.31 m

Steel depth$_{s2}$ ($h_{steel}$)=0.91 m

Steel depth$_{s3}$ ($h_{steel}$)=1.52 m

The pressure of the molten metal bath on each sampling mold at the desired sampling depth is determined as illustrated in Table 1 below:

| Bath Pressure Acting on Multi-Depth Sample Fill Tubes | | |
| --- | --- | --- |
| Sample mold # | Sampling depth (m) | Bath Pressure (kPa) |
| 1 | 0.31 | 28 |
| 2 | 0.91 | 70 |
| 3 | 1.52 | 112 |

Note:
Sampling depth is the depth below the slag-steel interface

The results of the calculation from Equation 3 indicate that with respect to the illustrated embodiment the multi-depth sampler needs to be pressurized with the purge gas at a pressure exceeding 112 kPa (i.e., 16.2 psi or 1.12 bar) in order to ensure that the sample mold 16 located deepest within the molten metal bath does not fill until the multi-depth sampling apparatus 1 is depressurized (e.g., turning off the gas source). As such, in some embodiments, the sampling apparatus 1 may be pressurized to 25 psi, to achieve a factor of safety to prevent premature filing of the sampling molds 10 until they are located at the desired locations within the molten metal. However, it should be understood that any amount of pressure may be calculated and utilized depending on the specific application of the sampling apparatus 1, the material being sampled, the depth from which the samples are being taken, and/or the like.

Figure 6:
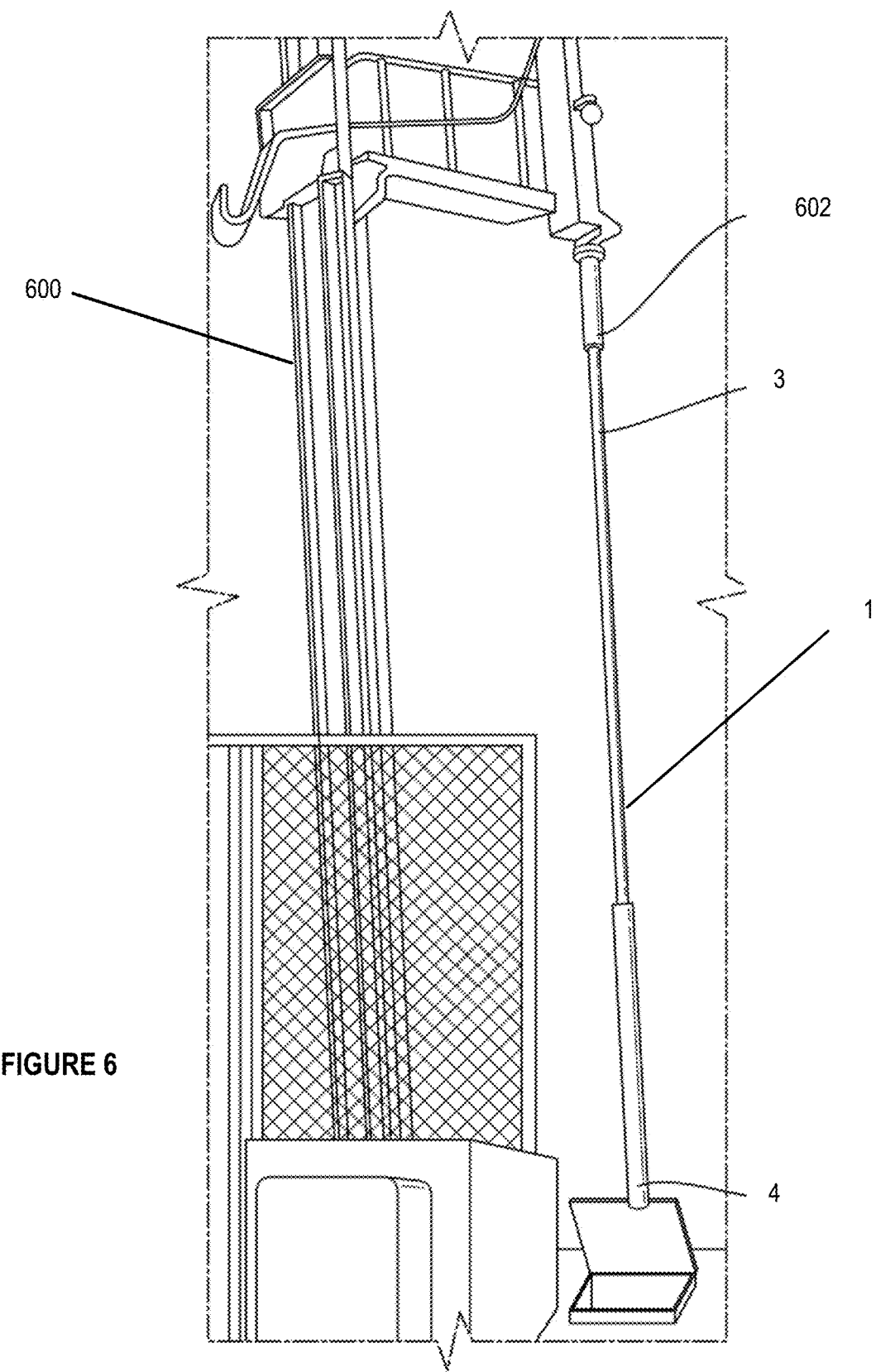
FIG. 6 illustrates a perspective view of the sampling apparatus being suspended over equipment before immersion, in accordance with embodiments of the present invention.
Figure 7:
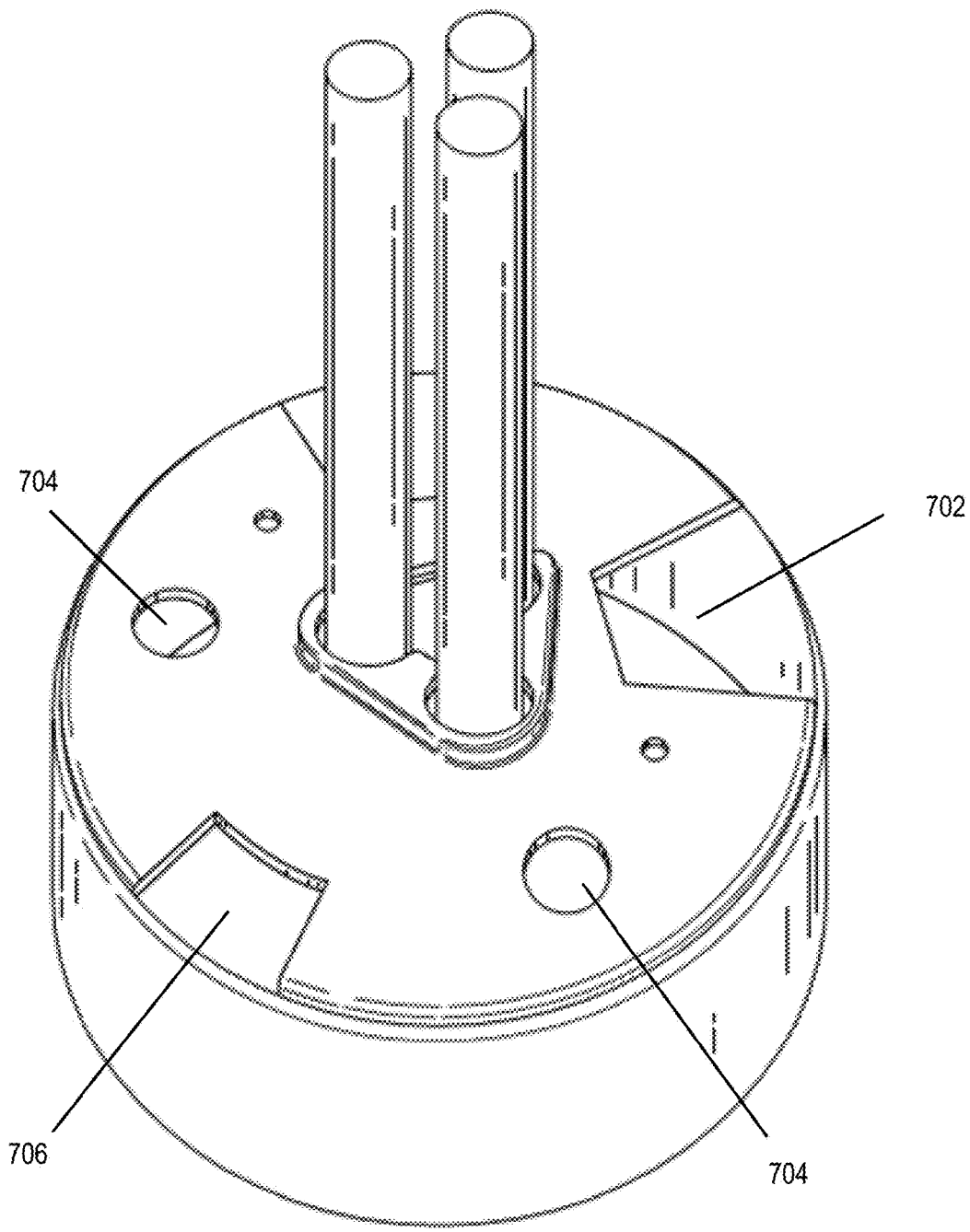
FIG. 7 illustrates a perspective view of a ladle in an LMF and access points through which the sampling apparatus may be utilized, in accordance with embodiments of the present invention.

Block 520 illustrates that the sampling apparatus 1 is suspended over an opening of steelmaking equipment having a molten metal bath. For example, as illustrated by FIG. 6, the sampling apparatus 1 may be suspended above an opening of a ladle metallurgy facility (LMF). FIG. 7 illustrates one example of an LMF in which the sampling apparatus 1 may be utilized. The sampling apparatus 1 may be suspended by an adjustable sampling apparatus support 600 and support arm 602 (e.g., by a stir lance arm, or another support) above the opening near where the one or more argon plugs are located at the bottom of the LMF, which are used for stirring the molten metal bath. It should be understood that the sampling apparatus 1 may be utilized at any other opening, such as the alloy addition opening 702, slag reading openings 704, robot sampler location 706, or any other opening in the ladle of the LMF, or in other locations for other equipment. Moreover, the sampling apparatus 1 may be immersed using equipment other than a stir lance arm depending on the equipment available.

Block 530 of FIG. 5 illustrates that the depth of immersion, time to turn off gas supply, time to let the sample molds 10 fill, and extraction time of the sampling apparatus 1 from the molten metal may all be set for automated control. In one example, the sampling apparatus support 600 and/or support arm 602 use a resolver to control depth, and as such the information is programmed into a control system (e.g., the lance arm control system, or the like) to control the immersion of the sampling apparatus 1, the release of argon pressure at the desired depth, as well as the time the sampler apparatus 1 stays in the LMF.

It should be understood that depending on when the sampling apparatus 1 is used within the molten metal in the LMF, the top surface of molten metal contained in the ladle of the LMF may be different. For example, during a high stir (e.g., when argon gas is used to stir molten metal bath), it is assumed that the motion of the slag layer adds inches (e.g., approximately 1, 2, 3 inches, or the like) to the depth on the sampling apparatus 1. As such, the programmed immersion depth of the sampling apparatus 1 may change based on when it is utilized within the LMF process, and/or when it is used within other types of processes.

In order to obtain a repeatable depth for the sampler apparatus 1 so that the samples are taken at the desired depths, additional test bars (e.g., the internal support 5) may be used to set the desired depth for lowering the sampling apparatus 1 into the molten metal. The test bars may be inserted using the sampling apparatus support 600 and support arm 602 (e.g., the stir lance arm, or the like) in order to determine the slag-steel depth and set the sampling apparatus support 600 and/or support arm 602 program (e.g., stir lance arm program, or the like) for the sampling apparatus 1. The test bars allow for the verification of the slag depth for positioning of the two or more sampling molds 10 within the sampling apparatus 1. As such, the test bar may be utilized to first identify the depth of the slag-molten metal interface by identifying burn-off on the test bar (e.g., inserting and removing the test bar to determine the slag-steel depth based on damage to the test bar). Measurements of the test bar burn-off may be taken and then applied to the sampling apparatus 1 before the sampling apparatus is immersed. After completion of the sampling process the sampling apparatus 1 may be examined to help verify the depth of the sampling molds 10 within the molten metal.

Block 540 illustrates that the sampling apparatus 1 is pressurized with the gas (e.g., argon gas, or other available gas) to the desired pressure. For example, returning to the example discussed herein, the sampling apparatus 1 may be pressurized to 25 psi. As previously discussed, the pressure may be changed based on when the sample is taken, where the sample is taken, how many samples are taken, or the like.

Block 550 illustrates that the sampling apparatus 1 is then immersed into the molten metal bath to the desired depth. For example, the sampling apparatus 1 may be immersed based on the programmed depth described in block 530. Due to the mold stops 10, the molten metal will not enter the sampling molds 10 (e.g., where mold stops are used). Also, with respect to any molds 10 that are unsealed (e.g., no mold stop, or the mold stops that have at least partially melted) the gas (e.g. argon gas, or the like) exiting or filling the one or more unsealed sampling molds 10 will not fill with molten metal. As previously discussed, the reason that one or more of the sampling molds 10 may be sealed is so that during the immersion, the pressurized purge gas cannot leak to atmosphere (causing depressurization of the sampling apparatus 1). Once the mold stops at least partially melt in the molten bath, the bath creates enough resistance to the flow of purge gas so that the sampling apparatus 1 does not depressurize.

FIG. 5 illustrates in block 560, that after being immersed to the desired depth the one or more sampling molds 10 that are sealed (e.g., the first mold 12, the second mold 14, and/or the third mold 16 that are sealed with mold stops 13, 15, 17, or other molds not illustrated) will be unsealed (e.g., the mold stops melt in the molten metal) and the pure gas may be turned off. Thereafter, the sampling molds 10 will fill with molten metal (e.g., after the gas is turned off). It should be understood that a portion, or all, of the mold stops 13, 15, 17 may melt before the purge gas is turned off, and as such the purge gas prevents the sampling molds (e.g., the first mold 12 and/or second mold 13) from filling with molten material before the purge gas is turned off. Alternatively, the purge gas may be turned off before the mold stops 13, 15, 17 melt, and as such the sampling apparatus 1 may be left in the molten metal for a time period to make sure the mold stops 13, 15, 17 have melted and the samples captured. In other embodiments, the third sampling mold 16 will fill with molten metal when the argon purge gas is turned off, while the first sampling mold 12, and/or second sampling mold 14 will fill with molten metal when the argon purge gas is turned off and the mold stops 13, 15 melt.

Block 570 illustrates that the sampling apparatus 1 is removed from the LMF with the samples filled with molten metal. For example, the sampling apparatus 1 may be removed after a pre-determined amount of time after the sampling apparatus 1 has been immersed and/or after purge gas is turned off. As previously discussed herein, the entire process from once the second end of the sampling apparatus 1 is immersed into the molten metal to when the second end is removed from the molten metal may take only 10, 7, 5, 3, or other like seconds. It should be understood that if the sampling apparatus 1 is left in the molten metal too long it may collapse on itself, may melt, the one or more cavities of the support structure 2 may be filled with molten metal, or the like. Once removed and cooled off, the samples may be removed from the sampling molds 10, and are analyzed to help to determine the cleanliness of the steel in the heat or determine any other process issues.

The sampling apparatus 1 and method of using the sampling apparatus 1 can be utilized to improve the steelmaking process, such as the steel cleanliness during secondary refining at the LMF. Improving the control of steel cleanliness through secondary steel refining can translate to a higher quality finished product. As such sampling the steel at different depths may play an important role in the determination and impact of the refining process on steel cleanliness. As illustrated in FIG. 7, samples of the molten steel may be taken at various points within the LMF process. For example, samples may be taken at the key steps of the LMF process 800, such as heat arrival/starting (S) 810, after alloying (A) 820, after desulfurization/the start of pre-rinse (R) 830, prior to calcium treatment/end of pre-rinse (C) 840, and/or after the end of post rinse/end of heat (E) 850.

Figure 9:
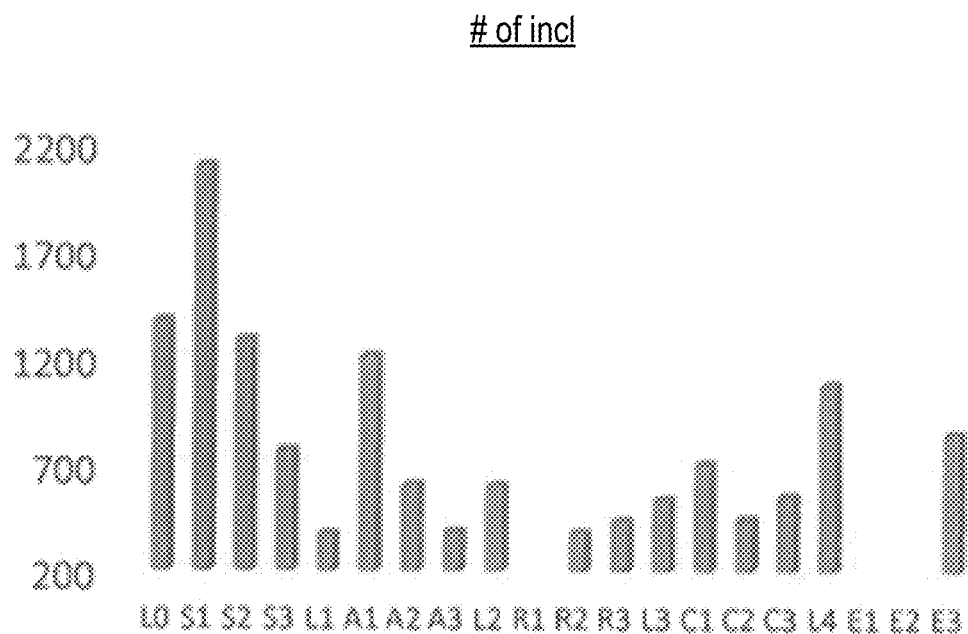
FIG. 9 illustrates a chart for the number of inclusions found during different LMF process steps at different depths utilizing the sampling apparatus described herein, in accordance with embodiments of the present invention.
Figure 10:
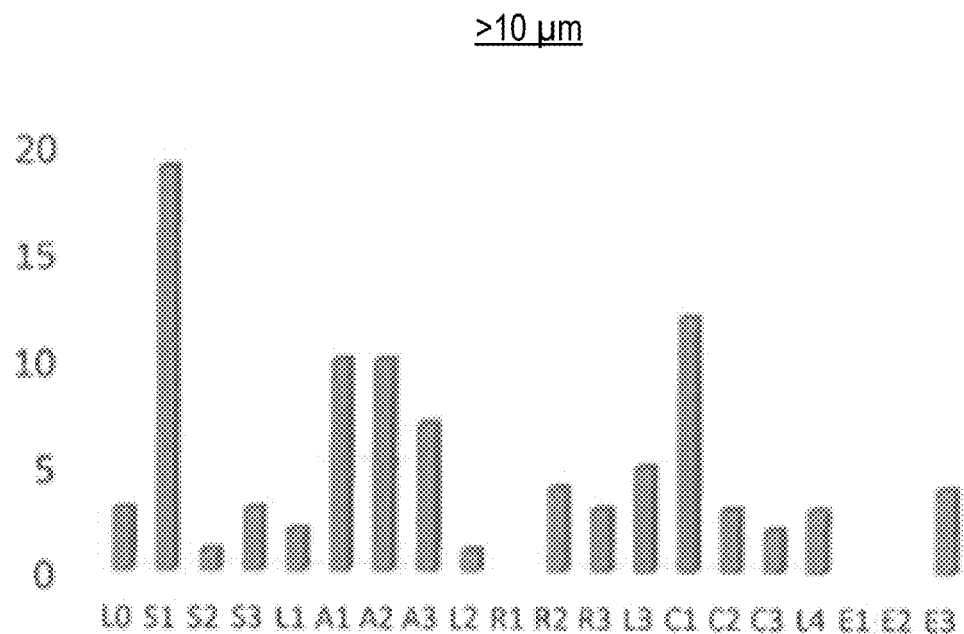
FIG. 10 illustrates a chart for the number of inclusions of a specific size found during different LMF process steps at different depths utilizing the sampling apparatus described herein, in accordance with embodiments of the present invention.

FIGS. 9 and 10 provide charts illustrating the number of inclusions and the size of inclusions found using a conventional sampler at one depth, and an embodiment of the multi-depth sampling apparatus 1 described herein at three depths. In the examples provided herein the samples were taken at two-foot increments down to a depth of approximately five feet into the ladle (e.g., 1 foot, 3 feet, and 5 feet). The data collected during sampling was used to depict a snap shot at each key process stage. The samples from the heat were collected and analyzed to determine differences in the ladle at different key process steps, as well as to compare against fundamental accepted knowledge at the LMF. The samples were analyzed by using a spectrometer for chemistry analysis as well as Automated Feature Analysis (AFA) analysis in an ASPEX SEM. All the results were compiled, and compared. It should be understood that the tests performed using the sampling apparatus 1 described herein are just one set of tests, and the sampling apparatus 1 may be utilized in a number of different ways in order to better understand the LMF process or other processes.

Figure 8:
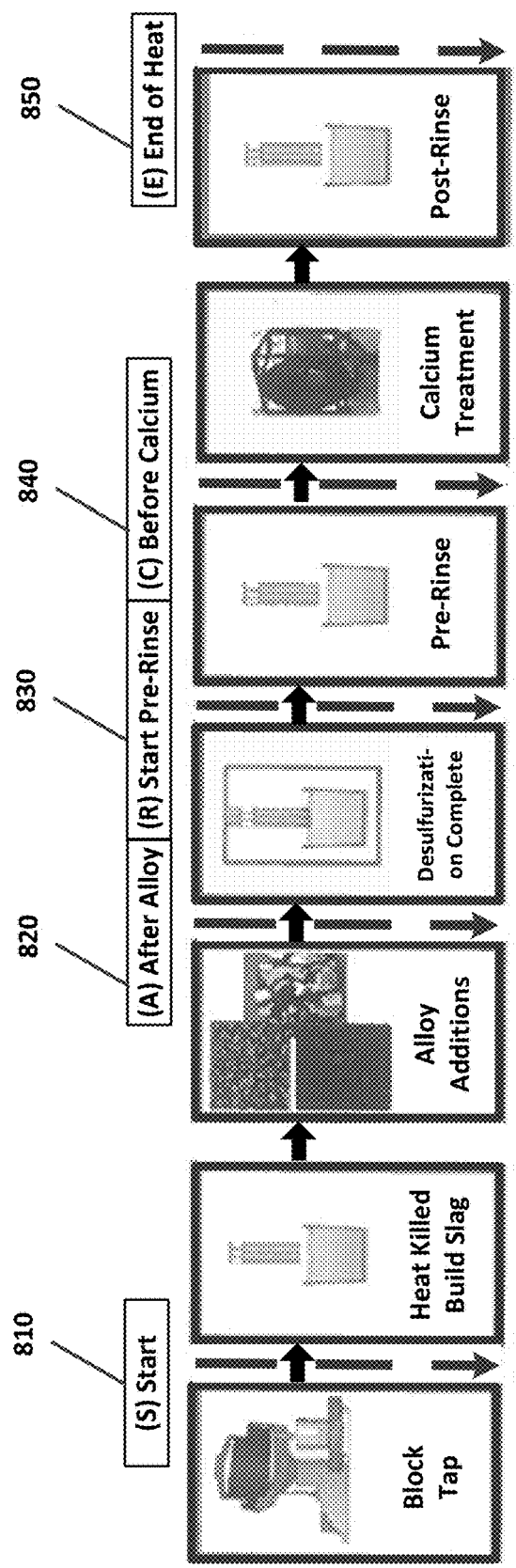
FIG. 8 illustrates a process flow of when the sampling apparatus may be used within the steelmaking process, in accordance with embodiments of the present invention.

The AFA analysis was conducted on all the samples from the sampling molds 10 to determine if there were any patterns of inclusion formation, and changes in the inclusions throughout the process steps and depths within the ladle and to compare the sampling apparatus 1 of the present invention with a conventional sampler. It is presumed that the slag-steel interface is where the most reactions occur. Therefore, the number of inclusions should decrease the further away from the slag-steel interface. FIG. 9 depicts the trend of decreasing inclusions as the LMF process progresses. It should be noted that the "L" type samples (i.e., L0, L1, L2, L3, L4, or the like) illustrated in FIGS. 9 and 10 were taken using a single sampling device at a single depth (e.g., the middle depth) at different stages of the process, and corresponded to the middle depth as the "X2" samples (S2, A2, R2, C3, E2, or the like) taken using the multi-depth sampler. It should be further understood that the "S" samples were taken at the start (S) of the process illustrated in FIG. 8; the "A" samples were taken after alloying (A) in the process illustrated in FIG. 8; the "R" samples were taken before pre-rinse (R) in the process illustrated in FIG. 8; the "C" samples were taken before calcium treatment (C) in the process illustrated in FIG. 8; and the "E" samples were taken at the end of the heat (E) in the process illustrated in FIG. 8. Moreover, the numbers 1, 2, and 3 for the S, A, R, C, and E samples correspond to the depths of the sampler in the multi-depth samplers (i.e., 1=upper, 2=middle, and 3=lower sampler depth). As illustrated in FIGS. 9 and 10 the number of inclusions and the inclusion sizes generally decreased with the depth of the samples, and the samples collected with the single depth sampler (e.g., at the middle depth) generally corresponded to the samples collected by the multi-depth sampler at the middle depth (e.g., "X2" locations). Some samples illustrated in the Figures were not tested because these samples did not capture testable samples.

Based on the analysis of the samples captured from the sampling apparatus 1, the manufacturing processes within the LMF may be improved by taking multi-depth samples upside and downside of the stir location (e.g., which may occur in one or more different locations within different types of ladles), at the alloy opening 702, or at other locations within the ladle to provide additional information for improving the ladle manufacturing processing. The sampling apparatus 1 may be utilized to gain a deeper understanding of the thermo-kinetic reactions taking place to better develop modeling of the molten metal in the ladle of the LMF. The sampling and modeling may help to determine improved slag viscosity, slag thickness, addition timing of alloys, potential effects of different alloying elements (e.g. Low Carbon Ferro Manganese vs High Carbon FerroManganese, FerroSilicon vs Silicon Manganese, or the like), as well as potential effects of certain elements on slag characteristics across the ladle in relation to how deep the slag proceeds into the bath.

As previously discussed above the sampling apparatus 1 and method of utilizing the sampling apparatus 1 may be utilized with other equipment in other steelmaking processes, or outside of the steelmaking industry. For example, while the sampling apparatus 1 has been described herein as being utilized for capturing samples of molten metal, the sampling apparatus 1 can be utilized in any application for which multiple samples need to be captured from a molten material (or liquid material). In particular, the sampling apparatus 1 may be utilized to capture samples from molten material that is being processed at an elevated temperature.

It should be understood that "operatively coupled," when used herein, means that the components may be formed integrally with each other, or may be formed separately and coupled together. Furthermore, "operatively coupled" means that the components may be formed directly to each other, or to each other with one or more components located between the components that are operatively coupled together. Furthermore, "operatively coupled" may mean that the components are detachable from each other, or that they are permanently coupled together.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations, modifications, and combinations of the just described embodiments can be configured without departing from the scope and spirit of the invention. Therefore, it is to be understood that, within the scope of the appended claims, the invention may be practiced other than as specifically described herein.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. Accordingly, the terms "a" and/or "an" shall mean "one or more."

What is claimed is:

1. A sampling apparatus, the apparatus comprising:
   one or more support structures having a first end and a second end, wherein the second end and at least a portion of the one or more support structures are configured for immersion within molten material;
   two or more sampling molds operatively coupled to the one or more support structures and configured for immersion within the molten material; and
   wherein the sampling apparatus is configured for operative coupling with a gas source in order to pressurize the sampling apparatus with a gas to prevent premature capture of the molten material samples in the two or more sampling molds and to capture the molten material samples in the two or more sampling molds at the same time when the gas source supply is stopped.

2. The sampling apparatus of claim 1, wherein the two or more sampling molds at least comprise:
   an upper sampling mold that is sealed with an upper mold stop;
   a lower sampling mold that is sealed with a lower mold stop; and
   wherein the upper sampling mold and lower sampling mold are immersed within the molten material, and capture molten material when the molten material at least partially melts the upper mold stop and the lower mold stop and the gas is stopped to allow flow of the molten material into the upper sampling mold and the lower sampling mold.

3. The sampling apparatus of claim 1, wherein the one or more support structures further comprise a refractory on the outside of the one or more support structures.

4. The sampling apparatus of claim 1, wherein the one or more support structures is a single support structure that is operatively coupled to the two or more sampling molds.

5. The sampling apparatus of claim 1, wherein the one or more support structures are at least two support structures operatively coupled together, and wherein each of the at least two support structures comprise at least a sampling mold.

6. The sampling apparatus of claim 1, wherein the molten material is molten metal.

7. The sampling apparatus of claim 6, wherein the two or more sampling molds at least comprise:
   an upper sampling mold that is sealed with an upper mold stop;
   a lower sampling mold that is unsealed; and
   wherein the upper sampling mold and the lower sampling mold are immersed within the molten material, and capture the molten material samples when the molten material at least partially melts the upper mold stop and the gas is stopped to allow flow of the molten material into the upper sampling mold and the lower sampling mold.

8. The sampling apparatus of claim 6, wherein the one or more sampling molds at least comprise:
   a first sampling mold;
   a second sampling mold;
   a third sampling mold; and
   wherein the third sampling mold is immersed deeper than the second sampling mold and the second sampling mold is immersed deeper than the first sampling mold, wherein the first sampling mold, the second sampling mold, and the third sampling mold capture molten steel samples when the gas source is stopped.

9. The sampling apparatus of claim 6, wherein the one or more support structures comprise:
   an internal support; and
   an external cover.

10. The sampling apparatus of claim 9, wherein the internal support comprises a metal tube, and the external cover comprises a paperboard tube.

11. A sampling apparatus, the apparatus comprising:
   one or more support structures having a first end and a second end;
   two or more sampling molds operatively coupled to the one or more support structures, wherein the two or more sampling molds comprise at least an upper sampling mold sealed with an upper mold stop and a lower sampling mold sealed with a lower mold stop;
   wherein the sampling apparatus is configured for operative coupling with a gas source in order to pressurize the sampling apparatus with a gas to prevent premature capture of samples from molten material in the two or more sampling molds;
   wherein the second end and at least a portion of the one or more support structures are configured for immersion within molten material such that the upper sampling mold and the lower sampling mold are submerged within the molten material at different depths; and
   wherein the two or more sampling molds capture the samples from the molten material when the molten material at least partially melts the two or more mold stops and the gas is stopped to allow flow of the molten material into the upper sampling mold and the lower sampling mold and at the same time.

12. The sampling apparatus of claim 11, wherein the two or more sampling molds further comprise a middle sampling mold sealed with a middle mode stop, wherein when immersed in the molten material the middle sampling mold is located at a depth between the upper sampling mold and the lower sampling mold.

13. A method for capturing molten material samples, the method comprising:
   pressurizing a sampling apparatus with a gas from a gas source, wherein the sampling apparatus comprises one or more support structures having a first end and a second end and two or more sampling molds operatively coupled to the one or more support structures;

immersing the second end of the sampling apparatus in a molten material such that the two or more sampling molds are immersed in the molten material at different depths;

depressurizing the sampling apparatus;

capturing samples of the molten material in the two or more sampling molds at the same time; and removing the sampling apparatus from the molten material.

14. The method of claim 13, wherein the molten material is molten metal.

15. The method of claim 13, wherein the two or more sampling molds at least comprise:

an upper sampling mold that is sealed with an upper mold stop;

a lower sampling mold that is sealed with a lower mold stop; and wherein the upper sampling mold and lower sampling mold are immersed within the molten material and capture molten material when the molten material at least partially melts the upper mold stop and the lower mold stop and the gas is stopped to allow flow of the molten material into the upper sampling mold and the lower sampling mold.

16. The method of claim 13, wherein the one or more sampling molds at least comprise:

an upper sampling mold that is sealed with an upper mold stop;

a lower sampling mold that is unsealed; and wherein the upper sampling mold and the lower sampling mold are immersed within the molten material and capture the molten material samples when the molten material at least partially melts the upper mold stop and the gas is stopped to allow flow of the molten material into the upper sampling mold and the lower sampling mold.

17. The method of claim 13, wherein the one or more sampling molds at least comprise:

a first sampling mold;

a second sampling mold;

a third sampling mold; and wherein the third sampling mold is immersed the deeper than the second sampling mold and the second sampling mold is immersed deeper than the first sampling mold, wherein the first sampling mold, the second sampling mold, and the third sampling mold capture the samples from the molten material when the gas is stopped.

18. The method of claim 13, wherein the one or more support structures is a single support structure that is operatively coupled to the two or more sampling molds, or are at least two support structures operatively coupled together and wherein each of the at least two support structures comprise at least a sampling mold.

19. The method of claim 13, wherein the one or more support structures further comprise an internal support and an external cover.

20. The method of claim 19, wherein the internal support comprises a metal tube and the external cover comprises a paperboard tube, and wherein the internal support prevents the sampling apparatus from collapsing on itself due to the pressure of the molten material.

* * * * *